(12) United States Patent
Merl

(10) Patent No.: US 12,377,598 B2
(45) Date of Patent: Aug. 5, 2025

(54) APPARATUS AND METHOD FOR TREATING CONTAINERS WITH IONISED AIR

(71) Applicant: KRONES AG, Neutraubling (DE)

(72) Inventor: Ulrich Merl, Teublitz (DE)

(73) Assignee: KRONES AG, Neutraubling (DE)

( * ) Notice: Subject to any disclaimer, the term of this patent is extended or adjusted under 35 U.S.C. 154(b) by 871 days.

(21) Appl. No.: 17/491,143

(22) Filed: Sep. 30, 2021

(65) Prior Publication Data

US 2022/0097285 A1 Mar. 31, 2022

(30) Foreign Application Priority Data

Sep. 30, 2020 (DE) ..................... 10 2020 125 478.4

(51) Int. Cl.
| | | |
|---|---|---|
| *B29C 49/42* | (2006.01) | |
| *A61L 2/14* | (2006.01) | |
| *B29C 49/46* | (2006.01) | |
| *B29C 71/00* | (2006.01) | |
| *B29L 31/00* | (2006.01) | |

(52) U.S. Cl.
CPC .......... *B29C 49/42418* (2022.05); *A61L 2/14* (2013.01); *B29C 49/42093* (2022.05); *B29C 49/4252* (2013.01); *B29C 49/46* (2013.01); *B29C 71/0009* (2013.01); *B29C 49/42095* (2022.05); *B29C 49/42414* (2022.05); *B29C 2949/0715* (2022.05); *B29L 2031/7158* (2013.01)

(58) Field of Classification Search
CPC ..................... B29C 49/42416; B29C 49/42418
See application file for complete search history.

(56) References Cited

U.S. PATENT DOCUMENTS

| | | | | |
|---|---|---|---|---|
| 8,746,172 B2* | 6/2014 | Krueger | .................... | A61L 2/14 |
| | | | | 118/723 R |
| 9,004,905 B2* | 4/2015 | Humele | .............. | B29C 49/6418 |
| | | | | 425/534 |
| 9,272,060 B2* | 3/2016 | Humele | .................. | B29C 49/42 |
| 9,327,442 B2* | 5/2016 | Engelhard | .............. | B29C 49/42 |
| 9,919,817 B2* | 3/2018 | Hayakawa | .......... | B29C 49/4252 |
| 10,112,338 B2* | 10/2018 | Aoki | ....................... | B29C 49/12 |

(Continued)

FOREIGN PATENT DOCUMENTS

| | | | | |
|---|---|---|---|---|
| DE | 10140906 | 3/2003 | .............. | B08B 6/00 |
| DE | 10 2011 107 772 | 1/2013 | ............. | B65B 55/04 |

(Continued)

OTHER PUBLICATIONS

Search Report issued in European Patent Appln. No. 21195857, dated Feb. 3, 2022, with English translation, 10 pages.

*Primary Examiner* — Atul P. Khare
(74) *Attorney, Agent, or Firm* — HAYES SOLOWAY P.C.

(57) ABSTRACT

Apparatus for treating plastic preforms, having a transport device which transports the plastic preforms along a predetermined transport path, having a first application device which loads the plastic preforms with a first flowable medium through their mouth during their transport along a first transport path section,
wherein
the apparatus has a second application device which acts upon the plastic preforms with a second flowable medium during their transport along a second transport path section through their mouth.

8 Claims, 2 Drawing Sheets

(56) References Cited

U.S. PATENT DOCUMENTS

| | | | |
|---|---|---|---|
| 10,350,816 B2 * | 7/2019 | Winzinger | ............... B65B 3/022 |
| 2009/0071104 A1 * | 3/2009 | Fischer | ..................... A61L 2/22 |
| | | | 53/426 |
| 2011/0209731 A1 * | 9/2011 | Mie | .......................... B29C 49/42 |
| | | | 134/171 |
| 2014/0325941 A1 * | 11/2014 | Knott | ..................... B29C 49/46 |
| | | | 53/167 |
| 2016/0193775 A1 * | 7/2016 | Lewin | ..................... B29C 49/12 |
| | | | 264/454 |
| 2018/0009646 A1 * | 1/2018 | Hayakawa | .......... B29C 49/4252 |

FOREIGN PATENT DOCUMENTS

| | | | | |
|---|---|---|---|---|
| DE | 102015111001 A1 * | 1/2017 | | |
| DE | 102018124287 A1 * | 4/2020 | ............... | A61L 2/07 |
| EP | 2987609 A1 * | 2/2016 | ............... | A61L 2/00 |

\* cited by examiner

APPARATUS AND METHOD FOR TREATING CONTAINERS WITH IONISED AIR

BACKGROUND OF THE INVENTION

The present invention relates to an apparatus and a method for treating containers and in particular plastic preforms.

In the beverage manufacturing industry, it has been known for a long time to heat plastic preforms and then to form them into a container such as a plastic bottle, for example, by means of a stretch blow-moulding machine. In this context, it is known from the applicant's internal prior art to act upon on or blow out such plastic preforms, for example also before heating them, with a flowable medium and in particular with filtered ionised air in order to clean them from the inside.

This procedure allows the plastic preforms to be cleaned, but not the killing of microbiological germs, which can also be found in particular inside these plastic preforms.

The present invention is therefore based on the object of also making it possible to kill off such germs in containers and in particular also in plastic preforms in a particularly process-economical manner.

SUMMARY OF THE INVENTION

An apparatus according to the invention for treating plastic preforms has a transport device which transports the plastic preforms along a predetermined transport path and a first application device which acts upon the plastic preforms, during their transport along a first transport path section of this transport path, through their mouth with a first flowable medium.

According to the invention, the apparatus has a second application device which pressurises the plastic preforms with a second flowable medium during their transport along a second transport path section (in particular the above-mentioned transport path) through their mouth. It is therefore proposed in the context of the invention that the plastic preforms are acted upon by the two—in particular different—flowable media during their transport with the apparatus. The flowable media can be gaseous media such as (compressed) air as well as liquid media such as liquids or vaporous media or the like.

Particularly preferably, the transport path sections are completely separated from each other, i.e. they do not overlap. Preferably, the second transport path section is essentially directly adjacent to the first transport path section.

In a particularly preferred embodiment, the transport device has a movable and, in particular, a rotatable carrier on which a plurality of holding devices for holding the plastic preforms are arranged. These holding devices are particularly preferably arranged individually, so that the plastic preforms can also be transported individually. Preferably, the plastic preforms are transported with a predetermined and, in particular, constant pitch with respect to each other.

In a preferred embodiment, each of these holding devices is assigned at least one and preferably exactly one application device.

In a further preferred embodiment, the application device has a providing unit which provides compressed air and, in particular, sterile compressed air. For example, a compressor device can be provided which generates compressed air.

Particularly preferably, the first providing unit also has filter devices, in particular sterile filters or cleaning devices for sterilising the air. For example, HEPA filters can be provided.

Particularly preferably, a compressor device is provided which generates compressed air and, particularly preferably, this compressor device is arranged in a stationary position. In this design, the pressurised medium, for example compressed air, is distributed via a rotary distributor to at least one application device and preferably to a plurality of application devices.

In a further preferred embodiment, at least one application device and/or a providing unit has an ionisation device for ionising air. In this way, ionised sterile air and in particular ionised and sterile compressed air can be provided to the individual plastic preforms.

In a further advantageous embodiment, at least one application device has a providing unit which provides a flowable sterilisation medium. In particular, but not exclusively, this can be hydrogen peroxide ($H_2O_2$). However, the use of peracetic acid is also conceivable.

In a further preferred embodiment, the first and second application devices have an application element which introduces the flowable medium into the plastic preforms (or which introduce the flowable medium into the plastic preforms). This can be, for example, a nozzle or the like, by means of which the respective substance is introduced into the preforms or plastic preforms. Preferably, this application element can also be fed to or introduced into the plastic preforms.

The application device is therefore the entire unit that serves to generate and also to supply the respective medium to the plastic preforms. The application element is understood to be the element which ultimately supplies the respective medium to the plastic preforms, such as a nozzle which projects into the mouths of the plastic preforms.

In a preferred embodiment, the first application device and the second application device use the same application element to act upon the plastic preforms with the respective flowable medium. In this case, the first substance, for example hydrogen peroxide, and also the second substance, for example sterile compressed air, are therefore fed into the plastic preforms via the same nozzle or the same application element.

In a further advantageous embodiment, the apparatus has a suction device for sucking a flowable medium (such as air) out of the plastic preform. For example, a substance containing contaminants can be sucked out of the plastic preform. This suction device can be a component of the first application device. In this way, it is possible that the application of the first flowable medium and the suction with regard to a specific plastic preform take place at the same time.

Particularly preferably, the apparatus is constructed in such a way that first suction is applied and then compressed air and/or a sterilisation medium such as hydrogen peroxide is applied.

In a further advantageous embodiment, the device has a switching device which switches over from acting upon the plastic preforms with the first flowable medium by means of the application elements to acting upon the plastic preforms with the second flowable medium by means of the application elements.

It is possible that the application of one or the other medium takes place depending on a certain position of the respective application device or the application element along the transport device. This means that the application of the respective media to the plastic preforms can also depend on a rotational position of the transport device, for example a rotatable carrier.

Preferably, the switching device has a plurality of valves which enable switching from the application of the first flowable medium to the application of the second flowable medium. A switching device of this type can be assigned to each application element. In this way, the individual pressurisation elements can be switched over individually.

In a further preferred embodiment, the apparatus has a distribution device for distributing the first flowable medium or the second flowable medium to the individual application devices and/or application elements. Such a distribution device can be provided both for the first flowable medium and for the second flowable medium. Particularly preferably, the distribution device is a so-called rotary distributor.

Furthermore, it is possible that a reservoir for the first and second flowable media is arranged stationary, and the respective flowable media are transferred (for example via rotary distributors) to the application elements and finally to the preforms.

In a further preferred embodiment, the transport device has a circumferential carrier, in particular a carrier that can be rotated with respect to an axis of rotation, on which a plurality of holding devices for holding the plastic preforms are arranged, wherein each holding device being assigned at least one, and preferably exactly one, application element for acting upon the plastic preforms with the flowable media. Preferably, these application elements are arranged above the rotatable carrier.

Particularly preferably, each holding device is assigned exactly one such application device or one such application. Advantageously, this application element can be fed onto the plastic preforms in a longitudinal direction of the plastic preforms.

In a further preferred embodiment, the transport device is a so-called clocking-in starwheel or a clocking-in device, which brings the plastic preforms fed in a row to a predetermined pitch.

It is possible that the plastic preforms are fed by means of a further feeding device, such as a preform chute. The transport device particularly preferably has recesses on its outer circumference, which serve to hold the plastic preforms. Particularly preferably, the plastic preforms are held between these recesses and a guide rail which runs outside the transport device. These recesses thus represent the respective holding devices.

In a further preferred embodiment, the application elements can also be moved and, in particular, reset in relation to the plastic preforms in a radial direction of the rotating carrier. In this way, it is also possible to transfer the plastic preforms to a further apparatus, such as a preform oven.

The present invention is further directed to an arrangement for treating plastic preforms with an apparatus of the type described above. Furthermore, the arrangement comprises an apparatus for sterilising plastic preforms or plastic containers arranged downstream of the apparatus in the transport device of the plastic preforms.

In a further preferred embodiment, the arrangement has a clean room within which at least one treatment step takes place, for example a forming of plastic preforms into plastic containers. Particularly preferably, at least the further sterilisation of plastic preforms or plastic containers with said downstream apparatus takes place within this clean room.

The apparatus described here is particularly preferably arranged outside this clean room and in particular in a so-called grey room in which a certain degree of cleaning is present but which does not yet reach the cleanliness levels applicable to the clean room.

Preferably, sluice devices are provided to feed the plastic preform(s) into the clean room. In a further preferred embodiment, the clean room has walls that delimit the clean room from a (non-sterile) environment. It is possible for one part of these walls to be movable relative to another part of these walls.

In a further preferred embodiment, the arrangement also has a heating device for heating plastic preforms. This heating device is also preferably arranged downstream of the apparatus described here in the transport direction of the plastic preforms. This heating device can, for example, be an infrared or microwave oven in which the plastic preforms are heated.

In a further preferred embodiment, the above-mentioned sterilisation device uses a flowable medium to sterilise the plastic preforms. In particular, this is the same sterilisation medium that the apparatus described here also uses. In particular, a sterilising medium such as $H_2O_2$ can be fed via a connecting line from a uniform evaporator both to the further apparatus and to the apparatus described here. An air rotary feedthrough may also be provided, as described above. Preferably, therefore, the sterilisation device comprises an evaporator for generating hydrogen peroxide.

Particularly preferably, the further apparatus for sterilising containers is an apparatus which sterilises the already manufactured containers.

The present invention is further directed to a method for treating plastic preforms, wherein a transport device transports the plastic preforms along a predetermined transport path and a first application device acts upon the plastic preforms during their transport along a first transport path section through their mouth with a first flowable medium.

According to the invention, a second application device acts upon the plastic preforms with a second flowable medium during their transport along the second transport path section through their mouth. Particularly preferably, the first flowable medium is ionised air and, in particular, sterile ionised air and, in particular, ionised sterile compressed air. Particularly preferably, the second flowable medium is a sterilisation medium and in particular hydrogen peroxide ($H_2O_2$). However, it would also be possible for the plastic preforms to first be acted upon to hydrogen peroxide and then to sterile air.

Particularly preferably, at least one application device comprises an ionisation device for ionising air and/or at least one application device ionises air.

Particularly preferably, the plastic preform is acted upon with the first or the second flowable medium during a transport of the plastic preforms and in particular during a transport of the plastic preforms along a circular transport path. However, a clocked transport is also conceivable.

In a further preferred method, a medium, and in particular air, is also extracted at least temporarily from the plastic preforms. Particularly preferably, this extraction takes place before the first flowable medium is applied.

In another preferred method, the plastic preforms are sterilised again in a further method step. This is particularly preferably done again with hydrogen peroxide. In a further preferred method, the plastic preforms are heated, in particular by means of an infrared oven.

In a further preferred method, the plastic preforms are separated by the transport device described here, i.e. they are spaced apart from each other in the transport direction.

Within the scope of the invention, it is therefore also proposed that a rinsing of the plastic preforms described here is also integrated into a sterilisation process of a further device, in particular a filler. In this context, a connecting line is particularly preferably provided which runs from a hydrogen peroxide evaporator to a rotary air feedthrough of the rinser of the apparatus described herein.

Preferably, as mentioned above, a second control circuit is set up for the sterilising agent, such as an $H_2O_2$ gas. Furthermore, a suction line is preferably laid from the AHU (Air Handling Unit) to the apparatus described here. This AHU is in particular a device which generates sterile air.

In a preferred method, the plastic preform is first transported via an infeed starwheel, such as a clocking-in starwheel, into the apparatus or treatment starwheel described here. Here, a nozzle first dips into the plastic preform and the suction is activated.

The plastic preform is then cleaned with ionised sterile air at a predetermined pressure and in particular a pressure that is higher than 2.0 bar, preferably higher than 2.5 bar and preferably higher than 3.0 bar. Particularly preferably, the pressure is lower than 10.0 bar, preferably lower than 8.0 bar, particularly preferably lower than 6.0 bar, preferably lower than 4.0 bar and preferably lower than 3.5 bar.

This cleaning can take place over a predefined area, for example a range of 12 coarse cycles. At the same time as this exposure, suction can also take place. In a preferred method, the sterile air is applied at the same time as the suction. In this way, dirt can be blown out of the plastic preforms and extracted.

The sterile air is then switched off and—preferably via a second control circuit—a switching valve, referred to above as switching device, is actuated. This switching valve applies $H_2O_2$ gas from an evaporator of a steriliser valve node into the plastic preform and in this way carries out a pre-treatment in it. In this way, the effectiveness and production reliability of the actual sterilisation in the treatment module or steriliser can be improved.

The invention described here thus provides cleaning and pre-treatment of plastic preforms, in particular in a transport starwheel. Furthermore, the sterilisation performance of the entire arrangement is improved. In addition, a higher production reliability is also achieved through a pre-treatment.

On the other hand, only minor modifications to existing technology are necessary compared to the state of the art.

BRIEF DESCRIPTION OF THE DRAWINGS

Further advantages and embodiments can be seen in the accompanying drawings.

In the drawings.

DETAILED DESCRIPTION OF THE INVENTION

Figure 1:
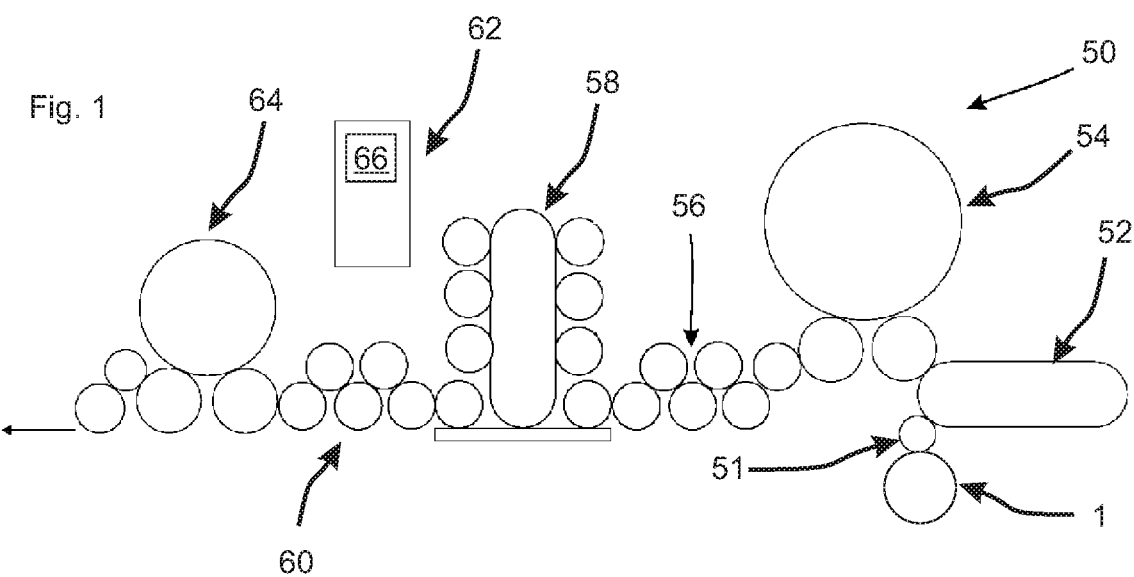
FIG. 1 shows a representation of an arrangement for producing containers.

FIG. 1 shows an illustration of an arrangement 50 for manufacturing containers. This has an oven 52 in which plastic preforms are heated. This oven is followed by a forming device 54 which forms the heated containers to plastic bottles. This forming device 54, which may be a stretch blow-moulding machine, for example, is followed by an optional first sterilisation device 56, which sterilises the containers.

The reference sign 58 indicates an (optionally available) coating device for coating the manufactured containers.

Reference 60 indicates a further sterilisation arrangement for sterilising the containers. This also has a providing device 62 which provides hydrogen peroxide gas instead of the sterilisation medium. The reference sign 66 indicates a vaporiser which is part of this providing device and which produces hydrogen peroxide vapour. This hydrogen peroxide vapour is used on the one hand for the further sterilisation device 60 and also for the apparatus described above.

The reference sign 64 indicates a filling device which fills the manufactured containers with a liquid, such as a beverage. This filling device is followed by a closing device which closes the containers with closures. A sterilisation device for sterilising these closures can also be provided.

The reference sign 1 refers to the apparatus according to the invention described here, which is used for rinsing and pre-sterilising the plastic preforms. This apparatus is connected to a feeding device which feeds the plastic preforms to the oven 52.

Figure 2:
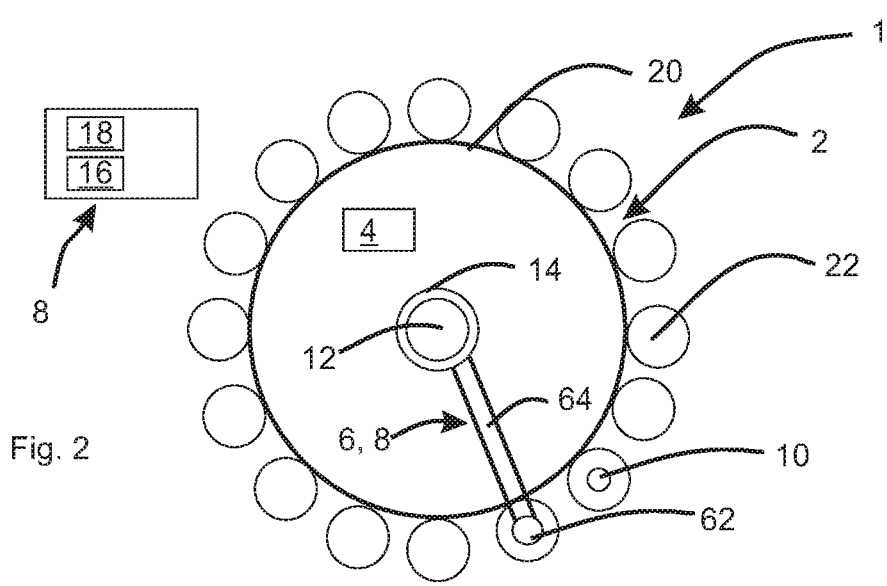
FIG. 2 shows a schematic representation of an apparatus according to the invention.

FIG. 2 shows a schematic representation of the apparatus 1 according to the invention, which has a transport device 2, such as a carrier wheel 20, on which a plurality of treatment stations are arranged. These stations each have holding devices 22 for holding plastic preforms 10.

The reference signs 6, 8 schematically refer to application devices which serve to act upon the plastic preforms 10 with a flowable medium by means of an application element 62. For this purpose, connecting lines 64 are also provided, which lead from a distributor device, for example rotary distributors 12, 14, to the application element. The application element 62 serves both to act upon the plastic preforms with the first flowable medium and to act upon the plastic preforms with the second flowable medium.

The reference sign 4 roughly schematically indicates a switching device by means of which it is possible to switch from acting upon the plastic preforms with the first flowable medium (in particular sterile air) to acting upon the plastic preforms with the second flowable medium.

The reference sign 8 also indicates a component of the providing device for the first flowable medium. This can, for example, have a compressor device 16 which provides compressed air. In addition, an ionisation device 18 can also be provided, which ionises the compressed air and which can thus be supplied to the application elements 62 via (not shown) connection lines.

Figure 3:
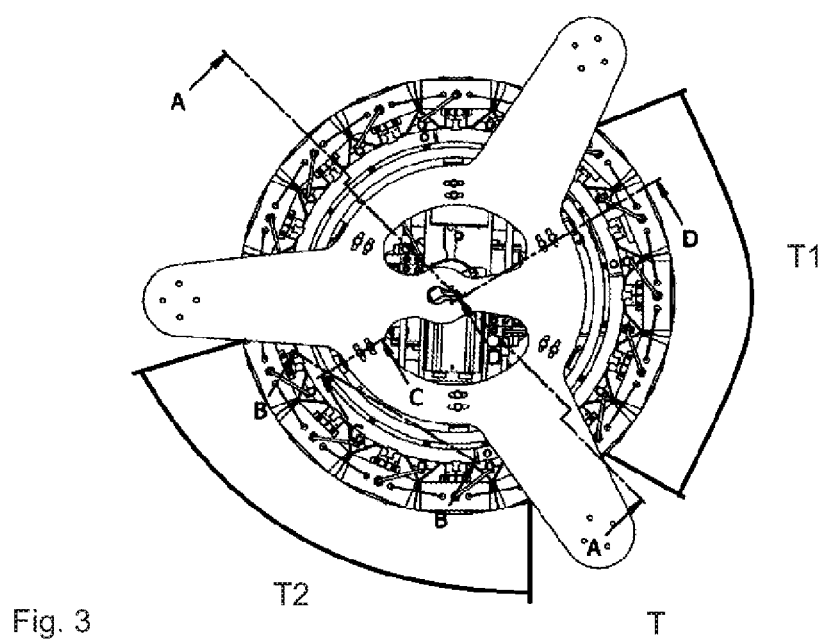
FIG. 3 shows a further view of an apparatus according to the invention.

FIG. 3 shows a top view of the application according to the invention. The reference sign T1 indicates a first transport path section along which the plastic preforms are acted upon with the first flowable medium and the reference sign T2 indicates a second transport path section along which the plastic preforms are acted upon with the second flowable medium. The entire transport path T of the plastic preforms is composed of the two transport path sections T1 and T2.

The applicant reserves the right to claim all features disclosed in the application documents as essential to the invention, provided they are individually or in combination new compared to the prior art. It is further pointed out that the individual figures also describe features which may be advantageous in themselves. The skilled person immediately recognises that a certain feature described in a figure can also be advantageous without adopting further features from this figure. Furthermore, the skilled person recognises that advantages can also result from a combination of several features shown in individual figures or in different figures.

The invention claimed is:

1. An apparatus for treating plastic preforms, said apparatus having a transport device which has a circulating carrier configured to transport the plastic preforms along a predetermined transport path, a first application device configured to act upon the plastic preforms with a first flowable medium through a mouth of the plastic preforms during transport of the plastic preforms along a first section of the transport path, and a second application device configured to act upon the plastic preforms with a second flowable medium during transport of the plastic preforms along a second section of the transport path through the mouth of the plastic preforms, wherein at least one of said first or said second application devices has an ionising device for ionising air, so that the first or second flowable medium is ionised air, wherein said first and said second application devices comprise an application element configured to introduce the first flowable medium and the second flowable medium into the plastic preforms, and wherein said first application device and said second application device are configured to use the application element to act upon the plastic preforms with the first flowable medium and the second flowable medium, further comprising a suction device configured for sucking off air or a substance containing contaminants out of the plastic preforms, wherein the application of the first flowable medium and the suction with regard to a specific one of the plastic preforms take place at the same time, and further comprising a switching device configured to switch over from acting upon the plastic preforms with the first flowable medium to acting upon the plastic preforms with the second flowable medium.

2. The apparatus according to claim 1, wherein said first application device has a compressed air unit configured to provide as the first flowable medium a compressed air to the first application device and/or said second application device has a compressed air unit configured to provide as the second flowable medium a compressed air to the second application device.

3. The apparatus according to claim 2, wherein said first application device comprises a providing unit configured to provide the first flowable medium as a sterilization medium to the first application device and/or said second application device comprises a providing unit configured to provide the second flowable medium as a sterilization medium to the second application device.

4. The apparatus according to claim 2, wherein the circulating carrier is rotatable with respect to an axis of rotation and on which a plurality of holding devices for holding the plastic preforms is arranged, wherein each of the holding devices has one application element for acting upon the plastic preforms with the first and second flowable medium.

5. The apparatus according to claim 1, wherein said first application device comprises a providing unit configured to provide the first flowable medium as a sterilization medium to the first application device and/or said second application device comprises a providing unit configured to provide the second flowable medium as a sterilization medium to the second application device.

6. The apparatus according to claim 1, wherein the circulating carrier is rotatable with respect to an axis of rotation and on which a plurality of holding devices for holding the plastic preforms is arranged, wherein each of the holding devices has one application element for acting upon the plastic preforms with the first and second flowable medium.

7. An arrangement for treating plastic preforms with an apparatus according to claim 1, the arrangement comprising a device configured for sterilising the plastic preforms or plastic containers formed therefrom arranged downstream of the apparatus in the transport direction of the plastic preforms.

8. A method for treating plastic preforms with an apparatus according to claim 1, wherein the transport device transports the plastic preforms along the predetermined transport path with the first application device acting upon the plastic preforms during their transport along the first transport path section through a mouth of the plastic preforms with the first flowable medium, and with the second application device acting upon the plastic preforms with the second flowable medium during their transport along the second transport path section through the mouth of the plastic preforms.

* * * * *